(12) United States Patent
Boymond et al.

(10) Patent No.: US 6,899,830 B1
(45) Date of Patent: May 31, 2005

(54) METHOD FOR PRODUCING GRIGNARD COMPOUNDS

(75) Inventors: Laure Boymond, Versailles (FR); Mario Rottländer, Marburg (DE); Gerard Cahiez, Paris (FR); Paul Knochel, Marburg (DE)

(73) Assignee: BASF, Ludwigshafen (DE)

( * ) Notice: Subject to any disclaimer, the term of this patent is extended or adjusted under 35 U.S.C. 154(b) by 0 days.

(21) Appl. No.: 09/647,069

(22) PCT Filed: Apr. 1, 1999

(86) PCT No.: PCT/EP99/02275

§ 371 (c)(1),
(2), (4) Date: Sep. 26, 2000

(87) PCT Pub. No.: WO99/51609

PCT Pub. Date: Oct. 14, 1999

(30) Foreign Application Priority Data

Apr. 14, 1998 (DE) .......................................... 198 16 414
Apr. 16, 1998 (DE) .......................................... 198 15 078
Aug. 12, 1998 (DE) .......................................... 198 36 408

(51) Int. Cl.$^7$ ................................................. C07F 3/02
(52) U.S. Cl. .................................. 260/665 G; 585/931
(58) Field of Search ....................... 260/665 R; 585/931

(56) References Cited

U.S. PATENT DOCUMENTS 4,254,030 A * 3/1981 Caporiccio et al. ......... 204/242
5,420,310 A * 5/1995 Ohno et al. .................. 549/458

FOREIGN PATENT DOCUMENTS

| DE | 1 964 405 | 7/1971 |
| DE | 25 41 438 | 3/1977 |
| DE | 19632643 | 1/1998 |
| GB | 1 310 596 | 12/1972 |
| WO | 97/05110 | 2/1997 |
| WO | WO 98/31676 | 7/1998 |

OTHER PUBLICATIONS

Hermkens, P. H. H.; Ottenheijm, H. C. J.; Rees, D. "Solid-Phase Organic Reactions: A Review of the Recent Literature" Tetrahedron. 1996, 52, 13, 4527–4554, see entire document, more particularly pp. 4530–4548.*

Solomons, Graham T. W. Organic Chemistry 5th Edition. New York: John Wiley & Sons, Inc. 1992, pp. 458–475.*

Minoura et al, Reaction of Poly(vinyl choride) with Magnesium and Grignard Reagents, 1969, Journal of Polymer Science: Part A–1, 7, 3245–3255.*

Boymond et al, Preparation of Highly Functionalized Grignard Reagents by an Iodine–Magnesium Exchange Reaction and its Application in Solid–Phase Synthesis, 1998, Angew. Chem. Int. E., 37(12), 1701–1703.*

Smith et al. "Improved synthesis of pentabromophenylmagnesium bromide and 1,2,4,5–tetrabromiphenylbis (magensium bromide)" J. of Organometallic Chem. vol. 33 (1971) pp. C21–C24.

Rakita et al. "Handbook of Gringard Reagents" (1996) pp. 1–50.

Chem. Abstracts vol. 86, No. 1 Abstr. No. 5381K.

Chem. Abstracts vol. 118, No. 17, Abstr. No. 168831a.

Posner, Org. React. vol. 22, 1975:253.

Tamao, J.Am.Chem.Socl, vol. 94, 1972: 4374.

Bull.Soc.Chim.FR., 1967:1520.

J.Organomet.Chem. vol. 113,1976:107.

Kabalka, Tetrahedron Lett,Bd.38,No. 33,1997:5777–5778.

Agnew.Chem.,vol. 108,1996:2436.

Evans et al., J.Chem.Soc. (A),1967: 1643–1648.

Angew.Chem.,vol. 81, 1969:93.

J.Organomet.Chem., vol. 113, 1976:107.

* cited by examiner

Primary Examiner—Andrew Wang
Assistant Examiner—Jon D Epperson
(74) Attorney, Agent, or Firm—Novak Druce & Quigg LLP

(57) ABSTRACT

The invention relates to a process for preparing Grignard compounds of the formula I. The invention additionally relates to compounds of the formula I and to polymer-bound compounds of the formula Ia. The invention further relates to the use of the process for preparing substance libraries and to the use of the compounds of the formulae I and Ia in chemical synthesis.

4 Claims, No Drawings

METHOD FOR PRODUCING GRIGNARD COMPOUNDS

The invention relates to a process for preparing Grignard compounds of the formula I. The invention additionally relates to compounds of the formula I and to polymer-bound compounds of the formula Ia. The invention further relates to the use of the process for preparing substance libraries and to the use of the compounds of the formulae I and Ia in chemical synthesis.

Grignard compounds are valuable intermediates in organic synthesis. They are among the most important classes of compounds in synthetic organic chemistry. Reaction thereof with electrophilic substances allows a wide variety of compounds to be prepared. A large number of syntheses in which Grignard compounds are used are disclosed in the literature (see: Handbook of Grignard-Reagents, Eds. G. S. Silverman, P. E. Rakita, Marcel Dekker, Inc., 1996). Grignard compounds have good reactivity with satisfactory chemoselectivity (see Posner G. H. Org. React., Vol. 22, 1975: 253, Lipshutz et al., Org. React., Vol. 41, 1992: 135, Luh T.-Y. Chem. Res., Vol 24, 1991: 257 or Tamao et al., J. Am. Chem. Soc., Vol. 94, 1972: 4374). DE 196 32 643 describes, for example, the synthesis of intermediates for angiotensin-II inhibitors via a Grignard compound. DE 25 41 438 and DE 19 64 405 describe the synthesis of fragrances by Grignard syntheses, for example for cosmetics.

The German application (file number 19709118.0) describes the synthesis of plant active principles by means of a Grignard compound which has thioalkyl ether or halogen substituents.

They are normally prepared as shown in scheme I, by reacting an appropriate alkyl or aryl halide with metallic magnesium or another magnesium source. The methods for this are known to the skilled worker and can be referred to in the Handbook of Grignard Reagents, Eds. G. S. Silverman, P. E. Rakita, Marcel Dekker, Inc., 1996.

Scheme I: Classical preparation of Grignard compounds

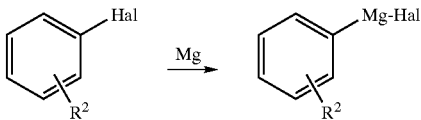

However, it is common to all these reactions that they are carried out under rather drastic conditions (temperatures >0° C., usually even at temperatures >+40° C.). These conditions do not, however, permit other functional groups, such as ester or nitrile moieties, which are able to react with a Grignard compound as electrophile to be retained in the molecule, because oligomerization, reduction or other side reactions would occur under these conditions.

Bull. Soc. Chim. Fr. 1967, 1520, Angew. Chem., Vol. 81, 1969: 293, J. Organomet. Chem., C21 G, 1971: 33, J. Organomet. Chem. Vol. 113, 1976: 107 and J. Organomet. Chem. Vol. 54, 1973: 123 describe the preparation of aryl Grignard compounds by halogen/magnesium exchange.

The conditions and reagents used therein do not, however, allow Grignard compounds with functional groups such as esters, nitrites or amides, which react with an electrophile, to be prepared.

Thus, for example, J. Organomet. Chem., Vol. 113, 1976: 107 describes the preparation of 2-pyridylmagnesium bromide (XI) starting from phenylmagnesium bromide (VII) and 2-chloropyridine (VIII) as shown in scheme II.

Scheme II: Synthesis of 2-pyridylmagnesium bromide

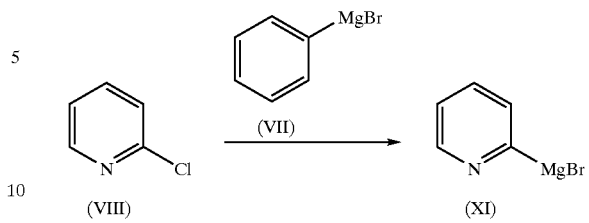

However, the reaction conditions are such that functional groups in the molecule would be immediately converted.

The simple preparation of Grignard compounds which contain functional groups which react with electrophiles has therefore not been disclosed to date.

It is an object of the present invention to provide a process for synthesizing Grignard compounds which contain other functional groups for many further types of chemical synthesis, which groups are able to react with electrophilic reagents.

We have found that this object is achieved by a process for preparing compounds of the general formula I

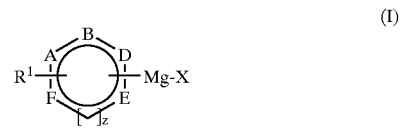

which comprises reacting compounds of the general formula II

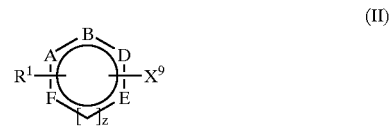

with compounds of the formula $R^4MgX$ (III) at temperatures below 0° C.,
where the substituents and variables in the formulae I, II and III have the following meanings:
Z=0,1
X=halogen such as Cl, Br, I or $R^2$
$x^a$=Br, I
A, B, D and E
 independently of one another CH, $CR^2$, N, P or $CR^3$
F=O, S, $NR^6$, $CR^2$ or $CR^3$ when z=0, or CH, $CR^2$, N, P or $CR^3$ when z=1,
it being possible for two adjacent variables A, B, D, E or F together to form another substituted or unsubstituted aromatic, saturated or partially saturated ring which has 5 to 8 atoms in the ring and which may contain one or more heteroatoms such as O, N, S, P, and not more than three of the variables A, B, D, E or F being a heteroatom.

It is preferred for not more than three of the variables A, B, D, E or F in the compounds of the formulae I, Ia and II to be nitrogen. If z=0, it is possible and advantageous for the ring to contain other heteroatoms such as oxygen or sulfur in addition to the nitrogen or in place of the nitrogen, it being possible for a maximum of one sulfur or oxygen atom to be present in the 5-membered ring. Examples which may be mentioned are 5-membered heterocycles with basic structures such as pyrrole, pyrazole, imidazole, triazole, oxazole, isoxazole, isothiazole, thiazole, furazan, oxadiazole, thiooxazole, thiophene or furan. Examples of 6-membered heterocycles which may be mentioned are rings with basic structures such as pyridine, pyrimidine, pyrazine, pyridazine or triazine. It is possible and advantageous, both for z=0 and for z=1, for the only heteroatom in the ring to be a phosphorus atom.

$R^1$=COOR$^2$, CN, CONR$^3$R$^{3'}$, halogen $R^2$=substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl, R$^5$, $R^3$=hydrogen, substituted or unsubstituted, branched or unbranched —OC$_1$–C$_{10}$-alkyl, —OC$_3$–C$_{10}$-cycloalkyl, —OC$_1$–C$_4$-alkylaryl, —OC$_1$–C$_4$-alkylhetaryl, R$^{3'}$ or R$^5$, $R^3$=hydrogen, substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl, R$^5$, $R^4$=substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl or halogen such as Cl, Br, I, preferably Br or I, $R^5$=a solid support, preferably a polymeric protective group, $R^6$=substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl, substituted or unsubstituted, branched or unbranched —(C=O)—C$_1$–C$_{10}$-alkyl, —(C=O)—C$_3$–C$_{10}$-cycloalkyl, —(C=O)—C$_1$–C$_4$-alkylaryl, —(C—O)—C$_1$–C$_4$-alkylhetaryl or —SO$_2$-aryl.

$R^1$ in the compounds of the formulae I and II is COOR$^2$, CN, CONR$^3$R$^3$, halogen such as F, Cl.

$R^2$ in the compounds of the formulae I and II is substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl or R$^5$.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of cycloalkyl radicals in the formula which may be mentioned are substituted or unsubstituted, branched or unbranched $C_3$–$C_{10}$-cycloalkyl radicals with 3 to 7 carbon atoms in the ring or ring system such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals may also contain heteroatoms such as S, N and O in the ring.

Radicals which may be mentioned as $C_1$–$C_4$-alkylaryl are substituted and unsubstituted, branched-chain or unbranched-chain $C_1$–$C_4$-alkylphenyl or $C_1$–$C_4$-alkylnaphthyl, such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

Alkylhetaryl radicals which may be mentioned are substituted and unsubstituted, branched-chain or unbranched-chain $C_1$–$C_4$-alkylhetaryl radicals which contain one or more nitrogen, sulfur and/or oxygen atoms in the ring or ring system.

$R^2$ can also be a solid support R$^5$ (see below for definition of the support).

Suitable substituents of the R$^2$ radicals mentioned are in principle, apart from ketones or aldehydes, all conceivable substituents, for example one or more substituents such as halogen such as fluorine, chlorine or bromine, cyano, nitro, amino, hydroxyl, alkyl, cycloalkyl, aryl, alkoxy, benzyloxy, phenyl or benzyl.

$R^3$ in the substituent R$^1$ is hydrogen, substituted or unsubstituted, branched or unbranched —OC$_1$–C$_{10}$-alkyl, —OC$_3$–C$_{10}$-cycloalkyl, —OC$_1$–C$_4$-alkylaryl, —OC$_1$–C$_4$-alkylhetaryl, R$^3$ or R$^5$.

—O-Alkyl radicals which may be mentioned are substituted or unsubstituted, branched or unbranched —OC$_1$–C$_{10}$-alkyl chains (=alkylhydroxamic acids linked via the oxygen). The $C_1$–$C_{10}$-alkyl chains in these —O-alkyl radicals have the following meanings: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of —O-cycloalkyl radicals in the radical R$^3$ which may be mentioned are substituted or unsubstituted, branched or unbranched —OC$_3$–C$_{10}$-cycloalkyl radicals with 3 to 7 carbon atoms in the ring or ring system, where the $C_3$–$C_{10}$-cycloalkyl radicals have the following meanings: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-ethyl-2-ethylcyclopropyl, cyclooctyl, cyclononyl or cyclodecyl. The cycloalkyl radicals may also contain heteroatoms such as S, N and O in the ring.

Radicals which may be mentioned as —O—C$_1$–C$_4$-alkylaryl are substituted and unsubstituted, branched-chain or unbranched-chain —O—C$_1$–C$_4$-alkylaryl, where the $C_1$–$C_4$-alkylaryl radicals have the following meanings: $C_1$–$C_4$-alkylphenyl or $C_1$–$C_4$-alkylnaphthyl radicals, such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

—O-Alkylhetaryl radicals which may be mentioned are substituted and unsubstituted, branched-chain or unbranched-chain —O—C$_1$–C$_4$-alkylhetaryl radicals which contain one or more nitrogen, sulfur and/or oxygen atoms in the ring or ring system.

$R^3$ can also be a solid support R$^5$ (see below for the definition of the support) or R$^{3'}$.

All the abovementioned radicals of the substituent R$^3$ are linked via the oxygen and form so-called hydroxamic acids in the case of the CONR$^3$R$^{3'}$ radical mentioned under R$^1$, otherwise ethers.

Suitable substituents of the said $R^3$ radicals are in principle, apart from ketones or aldehydes, all conceivable substituents, for example one or more substituents such as halogen such as fluorine, chlorine or bromine, cyano, nitro, amino, hydroxyl, alkyl, cycloalkyl, aryl, alkoxy, benzyloxy, phenyl or benzyl.

$R^{3'}$ in the substituent $R^1$ is hydrogen, substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl, $R^{3'}$ or $R^5$.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of cycloalkyl radicals in the formula which may be mentioned are substituted or unsubstituted, branched or unbranched $C_3$–$C_{10}$-cycloalkyl radicals with 3 to 7 carbon atoms in the ring or ring system such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals may also contain heteroatoms such as S, N and O in the ring.

Radicals which may be mentioned as $C_1$–$C_4$-alkylaryl are substituted and unsubstituted, branched-chain or unbranched-chain $C_1$–$C_4$-alkylphenyl or $C_1$–$C_4$-alkylnaphthyl, such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

Alkylhetaryl radicals which may be mentioned are substituted and unsubstituted, branched-chain or unbranched-chain $C_1$–$C_4$-alkylhetaryl radicals which contain one or more nitrogen, sulfur and/or oxygen atoms in the ring or ring system.

$R^{3'}$ can also be a solid support $R^5$ (see below for definition of the support).

Suitable substituents of the $R^{3'}$ radicals mentioned are in principle, apart from ketones or aldehydes, all conceivable substituents, for example one or more substituents such as halogen such as fluorine, chlorine or bromine, cyano, nitro, amino, hydroxyl, alkyl, cycloalkyl, aryl, alkoxy, benzyloxy, phenyl or benzyl.

$R^4$ in the formula $R^4MgX$ (III) is substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl or halogen such as chlorine, bromine or iodine, preferably bromine or iodine.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of cycloalkyl radicals in the formula which may be mentioned are substituted or unsubstituted, branched or unbranched $C_3$–$C_{10}$-cycloalkyl radicals with 3 to 7 carbon atoms in the ring or ring system such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals may also contain heteroatoms such as S, N and O in the ring.

Radicals which may be mentioned as $C_1$–$C_4$-alkylaryl are substituted and unsubstituted, branched-chain or unbranched-chain $C_1$–$C_4$-alkylphenyl or $C_1$–$C_4$-alkylnaphthyl, such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

Alkylhetaryl radicals which may be mentioned are substituted and unsubstituted, branched-chain or unbranched-chain $C_1$–$C_4$-alkylhetaryl radicals which contain one or more nitrogen, sulfur and/or oxygen atoms in the ring or ring system.

Suitable substituents of the $R^4$ radicals mentioned are in principle, apart from ketones or aldehydes, all conceivable substituents, for example one or more substituents such as halogen such as fluorine, chlorine or bromine, cyano, nitro, amino, hydroxyl, alkyl, cycloalkyl, aryl, alkoxy, benzyloxy, phenyl or benzyl.

$R^6$ is substituted or unsubstituted, branched or unbranched $c_1$–$C_{10}$-alkyl, $C_3$–$C_{10}$-cycloalkyl, $C_1$–$C_4$-alkylaryl, $C_1$–$C_4$-alkylhetaryl, substituted or unsubstituted, branched or unbranched —(C=O)—$C_1$–$C_{10}$-alkyl, —(C=O)—$C_3$–$C_{10}$-cycloalkyl, —(C=O)—$C_1$–$C_4$-alkylaryl, —(C—O)—$C_1$–$C_4$-alkylhetaryl or —$SO_2$-aryl.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of cycloalkyl radicals in the formula which may be mentioned are substituted or unsubstituted, branched or unbranched $C_3$–$C_{10}$-cycloalkyl radicals with 3 to 7 carbon atoms in the ring or ring system such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals may also contain heteroatoms such as S, N and O in the ring.

Radicals which may be mentioned as $C_1$–$C_4$-alkylaryl are substituted and unsubstituted, branched-chain or unbranched-chain $C_1$–$C_4$-alkylphenyl or $C_1$–$C_4$-alkylnaphthyl, such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

Alkylhetaryl radicals which may be mentioned are substituted and unsubstituted, branched-chain or unbranched-chain $C_1$–$C_4$-alkylhetaryl radicals which contain one or more nitrogen, sulfur and/or oxygen atoms in the ring or ring system.

—(C—O)-Alkyl radicals which may be mentioned are substituted or unsubstituted, branched or unbranched —(C=O)—$C_1$–$C_{10}$-alkyl chains (=linked via the carbon to which the oxygen is attached by the double bond). The $C_1$–$C_{10}$-alkyl chains in these —(C=O)-alkyl radicals have the following meanings: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of —(C=O)-cycloalkyl radicals in the $R^6$ radical which may be mentioned are substituted or unsubstituted, branched or unbranched —(C—O)—$C_3$–$C_{10}$-cycloalkyl radicals with 3 to 7 carbon atoms in the ring or ring system, where the $C_3$–$C_{10}$-cycloalkyl radicals have the following meanings: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals may also contain heteroatoms such as S, N and O in the ring.

Radicals which may be mentioned as —(C—O)—$C_1$–$C_4$-alkylaryl are substituted and unsubstituted, branched-chain or unbranched-chain —(C=O)—$C_1$–$C_4$-alkylaryl, where the $C_1$–$C_4$-alkylaryl radicals have the following meanings: $C_1$–$C_4$-alkylphenyl or $C_1$–$C_4$-alkylnaphthyl radicals, such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

—(C=O)-Alkylhetaryl radicals which may be mentioned are substituted and unsubstituted, branched-chain or unbranched-chain —(C=O)—$C_1$–$C_4$-alkylhetaryl radicals which contain one or more nitrogen, sulfur and/or oxygen atoms in the ring or ring system.

All said —(C=O) radicals are linked via the carbon attached to the oxygen via a double bond.

$R^6$ radicals which may also be mentioned are —$SO_2$-aryl radicals such as —$SO_2$-phenyl or —$SO_2$-naphthyl. Linkage takes place via the 502 radical.

Suitable substituents for the said $R^6$ radicals are in principle, apart from ketones or aldehydes, all conceivable substituents, for example one or more substituents such as halogen such as fluorine, chlorine or bromine, cyano, nitro, amino, hydroxyl, alkyl, cycloalkyl, aryl, alkoxy, benzyloxy, phenyl or benzyl.

The compounds of the formulae I, Ia and II are aromatic compounds.

The reaction in the process according to the invention is advantageously carried out by reacting the compound II advantageously in an inert, aprotic solvent, for example ethers such as tetrahydrofuran (=THF), diethyl ether, dioxane, dimethoxyethane or methyl tert-butyl ether (=MTB), at temperatures below 0° C., preferably below –10° C., particularly preferably below –15° C., very particularly preferably at –40° C. or below, with a compound of the general formula $R^4$MgX (III) to give a compound of the formula I. It is possible in principle to use all compounds of the formula $R^4$MgX known to the skilled worker for preparing the Grignard compound, and diisopropylmagnesium or dicyclopentylmagnesium is preferably used. The reaction can generally be carried out in a range from –70° C. to 0° C.

Reactions at higher temperatures, for example at 25° C., lead to by-products and thus distinctly lower yields.

Under these mild conditions, the halogen/magnesium exchange takes place without the Grignard compounds of the formula II (see above) which are formed reacting with the other functional groups present in the molecule. The compounds react with the electrophile (see examples in Table I) only in the required manner. Conversion with the electrophile greater than 70%, preferably greater than 80%, particularly preferably greater than 85%, very particularly preferably greater than 90%, are possible in this way.

The reaction is usually complete within 10 hours, preferably within 5 hours, particularly preferably within 4 hours.

A variant of the process comprises employing not the dialkylmagnesium compound (III with $R^4$=$R^2$=X) directly, but an easily obtainable Grignard compound X=Hal which then, under the reaction conditions, forms in accordance with the Schlenk equilibrium the dialkylmagnesium compound which then undergoes the actual reaction.

A particular advantage of this process is that esters of bound alcohols, preferably alcohols bound to polymers, also undergo the halogen/magnesium exchange in the required manner. (Examples in Table II).

The linkage of the compounds of the formula I can in this case take place via a solid support (=$R^5$) like those known from solid-phase peptide synthesis. Supports which can be used can consist of a large number of materials as long as they are compatible with the synthetic chemistry used, it being possible for the size, size distribution and shape of the supports to vary widely depending on the material. Spherical particles are preferred and advantageously have a homogeneous size distribution.

Examples of suitable solid supports are ceramic, glass, latex, functionalized crosslinked polystyrenes, polyacrylamides, silica gels or resins.

In order to make attachment of the reactant and elimination of the synthetic product after the synthesis possible, the support must be suitably functionalized or provided with a linker which has an appropriate functional group which makes it possible to attach the compounds according to the invention. Examples of suitable and preferred supports and support-linker conjugates are chlorobenzyl-resin (Merrifield resin), Rink resin (Novabiochem), Sieber resin (Novabiochem), Wang resin (Bachem), Tentagel resins (Rapp-Polymere), Pega resin (Polymer Laboratories) or polyacrylamides. Hydroxybenzyl-resin (Wang resin) is particularly preferred as support. Very particularly preferred polymeric supports and protective groups are, for example, triphenylmethyl, p-benzyloxybenzyl alcohol, 4-(2',4'-dimethoxyphenyl(hydroxy)methyl)phenoxypolystyrene or 4-(2',4'-dimethoxyphenylmethyl)phenoxypolystyrene.

The attachment of the compound to the support or polymeric support takes place by reactions which are known to the skilled worker and which are to be found, for example, in the Review by Balkenhohl et al. (Angew. Chem., Vol. 108, 1996: 2436) and the literature cited therein. In the case of Wang resin, the attachment can take place, for example, via an ester. The latter can be eliminated from the resin with, for example, trifluoroacetic acid after the synthesis is complete.

It is possible in this way to utilize the advantages of solid-phase synthesis, namely the automatic carrying out and workup of the reaction by simple washing and filtering. It is thus possible to produce substance libraries easily by use of the process according to the invention.

This means that this reaction is very suitable for generating substance libraries according to the principles of combinatorial chemistry or HSA (Angew. Chem., Vol. 108, 1996: 2436) by first carrying out the halogen/magnesium exchange on a polymer-linked precursor and then reacting the latter with a large number of electrophiles (in one vessel to generate mixtures).

After washing and filtering, the target products are then detached from the polymer under conditions suitable for cleavage of the linker bonding.

The compounds according to the invention of the formulae I or Ia ($=R^5=$solid support, preferably polymeric support) can advantageously be used in chemical synthesis as starting materials or intermediates which can be employed in various subsequent reactions. Examples which may be mentioned here are carotenoid, vitamin or active ingredient syntheses, such as active ingredients in the drugs or crop protection sector.

The following examples are intended to illustrate the process without meaning to restrict the method:

EXAMPLES

A Preparation of Ethyl 4-(α-hydroxybenzyl) benzoate

A solution of 552 mg (2 mmol) of ethyl 4-iodobenzoate in 20 ml of THF was cooled to −40° C. and 1.06 mmol of diisopropylmagnesium in methyl tert-butyl ether were added. After 1 h at −40° C. 233 mg (2.2 mmol) of benzaldehyde were added. After 3 h, the reaction mixture was hydrolyzed and the org. phase was concentrated. Chromatography of the crude product with 4/1 pentane/ether afforded 460 mg (90%) of the alcohol.

Table I shows the results of analogous reactions with various electrophiles.

The starting compounds (Grignard compounds) were prepared via iodine/magnesium exchange within half an hour to one hour. The temperature of the reaction solution was between −25 and −40° C. Good conversions were achievable at this temperature. The yields can be increased by using cPent2Mg for the iodine/magnesium exchange reaction (see data in parentheses).

The conversions stated in Table I relate to chemically pure final product. The allylation reactions were carried out in the presence of CuCN×2 LiCl (10 mol %) (see, for example, Nos. 4–7 and 9, 10 and 13).

TABLE I

Preparation of Grignard compounds and reaction with electrophiles.

| No. | Aryl halide | Electrophile | Product | Yield (%) |
|---|---|---|---|---|
| 1 | I—C6H4—CO2tBu | PhCHO | Ph—CH(OH)—C6H4—CO2tBu | 91 (94) |
| 2 | I—C6H4—CN (meta) | PhCHO | Ph—CH(OH)—C6H4—CN (meta) | 89 |
| 3 | I—C6H4—CO2Et | PhCHO | Ph—CH(OH)—C6H4—CO2Et | 90 |

TABLE I-continued

Preparation of Grignard compounds and reaction with electrophiles.

| No. | Aryl halide | Electrophile | Product | Yield (%) |
|---|---|---|---|---|
| 4 | 4-I-C6H4-CON(piperidine) | allyl bromide | 4-allyl-C6H4-CO2N(piperidine) | 81 |
| 5 | 4-I-C6H4-CN | allyl bromide | 4-allyl-C6H4-CN | 75 |
| 6 | 1-iodonaphthalene | allyl bromide | 1-allylnaphthalene | 80 (87) |
| 7 | 4-I-C6H4-Br | allyl bromide | 4-allyl-C6H4-Br | 79 |
| 8 | 4-I-C6H4-Br | PhCHO | Ph(HO)HC-C6H4-Br | 93 |
| 9 | 2-I-C6H4-Br | allyl bromide | 2-allyl-C6H4-Br | 79 |
| 10 | 4-I-C6H4-C(O)N(piperidine) | allyl bromide | 4-allyl-C6H4-C(O)N(piperidine) | 81 |
| 11 | 4-I-C6H4-CN | PhCHO | Ph(HO)HC-C6H4-CN | 94 |
| 12 | 4-I-C6H4-CN | HexCHO | Hex(HO)HC-C6H4-CN | 74 |
| 13 | 2-I-C6H4-NC | allyl bromide | 2-allyl-C6H4-NC | 89 |

B. Preparation of Grignard Compounds on a Polymeric Support and Reaction with Electrophiles 100 mg of Wang resin were mixed with 70 mmol of 4-iodobenzoic acid and 2 ml of THF and cooled to −35° C. 0.7 ml (0.51 mmol) of a 0.73 M solution of diisopropylmagnesium in ThF was added dropwise and, after 15 min., 0.7 ml of a 1 M solution of CuCN*2LiCl in THF. Then 0.3 ml of allyl bromide was added and the mixture was stirred for 1 h.

Filtration and washing provided the polymer-bound product, which was detached from the polymer under standard conditions (trifluoroacetic acid).

The substances listed in Table II were prepared analogously. The yield of free product was usually 90% or more (see data in the table, column 5).

TABLE II

Preparation of Grignard compounds and reaction with electrophiles on a solid support.

| No. | Aryl halide | Electrophile | Product (polymer-bound) | Product (eliminated from the polymer) |
|---|---|---|---|---|
| 1 | I–C6H4–CO2–P (para) | allyl bromide (CH2=CH–CH2–Br) | allyl–C6H4–CO2–P | allyl–C6H4–CO2H  >90 |
| 2 | I–C6H4–CO2–P (para) | CH2=C(CO2Et)–CH2–Br | EtCO2–C(=CH2)–CH2–C6H4–CO2–P | EtCO2–C(=CH2)–CH2–C6H4–CO2H  >90 |
| 3 | I–C6H4–CO2–P (para) | PhCHO | Ph–CH(OH)–C6H4–CO2–P | Ph–CH(OH)–C6H4–CO2H  >90 |
| 4 | I–C6H4–CO2–P (para) | TosCN | NC–C6H4–CO2–P | NC–C6H4–CO2H  >90 |
| 5 | Br–(2-thienyl)–CO2–P | TosCN | NC–(2-thienyl)–CO2–P | NC–(2-thienyl)–CO2H  >90 |
| 6 | Br–(2-thienyl)–CO2–P | CH2=C(CO2Et)–CH2–Br | EtCO2–C(=CH2)–CH2–(2-thienyl)–CO2–P | EtCO2–C(=CH2)–CH2–(2-thienyl)–CO2H  >90 |
| 7 | I–C6H4–CO2–P (para) | PhSSPh | Ph–S–C6H4–CO2–P | Ph–S–C6H4–CO2H  <90 |
| 8 | I–C6H4–CO2–P (meta) | PhSSPh | Ph–S–C6H4–CO2–P (meta) | Ph–S–C6H4–CO2H (meta)  <90 |

TABLE II-continued

Preparation of Grignard compounds and reaction with electrophiles on a solid support.

| No. | Aryl halide | Electrophile | Product (polymer-bound) | Product (eliminated from the polymer) |
|---|---|---|---|---|
| 9 | (3-iodobenzoate-P) | TosCN | (3-cyanobenzoate-P) | (3-cyanobenzoic acid) >90 |
| 10 | (5-bromothiophene-2-carboxylate-P) | allyl bromide | (5-allylthiophene-2-carboxylate-P) | (5-allylthiophene-2-carboxylic acid) >90 |
| 11 | (5-bromofuran-2-carboxylate-P) | TosCN | (5-cyanofuran-2-carboxylate-P) | (5-cyanofuran-2-carboxylic acid) >90 |

We claim:

1. A process for preparing compounds of the general formula I

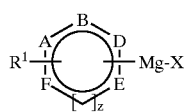

(I)

which comprises reacting compounds of the general formula II

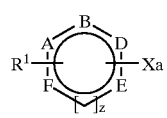

(II)

with compounds of the formula $R^4MgX$ (III) at temperatures below 0° C., where the substituents and variables in the formulae, I, II and III have the following meanings:

wherein Z is 0 or 1
wherein X is halogen or $R^2$
wherein $X^a$ is Br, or I
wherein A, B, D and E
independently of one another are CH, $CR^2$, N, P or $CR^3$
wherein F is O, S, $NR^6$, $CR^2$, or $CR^3$ when z=0, or CH, $CR^2$, N, P or $CR^3$ when z=1,
wherein two adjacent variables A, B, D, E or F together optionally form another substituted or unsubstituted aromatic saturated or partially saturated ring which has 5 to 8 atoms in the ring and which may contain one or more heteroatoms such as O, N, S, P, and not more than three of the variables, A, B, D, E or F being a heteroatom, wherein $R^1$ is $COOR^2$, CN, $CONR^3R^3$, or Halogen wherein $R^2$ is substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl, or $R^5$, wherein $R^3$ is hydrogen, substituted or unsubstituted, branched or unbranched —$OC_1$–$C_{10}$-alkyl, —$OC_3$–$C_{10}$-cycloalkyl, —$OC_1$–$C_4$-alkylaryl, —$oC_1$–$C_4$-alkylhetaryl, $R^3$ or $R^5$, wherein $R^3$ is hydrogen, substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl, or $R^5$, wherein $R^4$ is substituted or unsubstituted, branced or unbranched $C_1$–$C_{10}$-alkyl, $C_3$–$C_{10}$-cycloalkyl, $C_1$–$C_4$-alkylaryl, $C_1$–$C_4$-alkylhetaryl, or halogen, wherein $R^5$ is a solid support, wherein $R^6$ is substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylhetaryl, substituted or unsubstituted, branched or unbranched —(C=O)—$C_1$–$C_{10}$-alkyl, —(C=O)—$C_3$–$C_{10}$-cycloalkyl, —(C=O)—$C_1$–$C_4$-alkylaryl, —(C=O)—$C_1$–$C_4$-alkylhetaryl or —$SO_2$—aryl where the process is caried out on a solid support ($R^5$).

2. A process as claimed in claim 1, which is carried out in an inert aprotic solvent.

3. A process as claimed in claim 1, which is carried out at temperatures below –15° C.

4. A process as claimed in claim 1, wherein the reaction to give compounds of the formula I as set forth in claim 1 is complete within 10 hours.

* * * * *